United States Patent [19]

Haas et al.

[11] Patent Number: 5,760,098

[45] Date of Patent: Jun. 2, 1998

[54] PROCESS FOR PRODUCING LOW-EMISSION POLYURETHANE MOLDINGS AND COMPOSITE BODIES AND THEIR USE

[75] Inventors: Peter Haas, Haan; Ulrich Liman, Langenfeld, both of Germany

[73] Assignee: Bayer Aktiengesellschaft, Leverkusen, Germany

[21] Appl. No.: 688,885

[22] Filed: Jul. 31, 1996

[30] Foreign Application Priority Data

Aug. 10, 1995 [DE] Germany .................. 195 29 412.2

[51] Int. Cl.[6] .................................................. C08G 18/18

[52] U.S. Cl. .................. 521/125; 264/45.1; 264/45.8; 264/46.5; 156/77; 156/78; 156/79; 428/424.2; 428/424.4; 428/424.6; 428/424.7; 521/128; 521/129; 521/130; 521/157; 528/49; 528/53; 528/57; 528/84

[58] Field of Search .................. 528/49, 57, 53, 528/84; 521/125, 128, 130, 129, 157; 156/77, 78, 79; 428/424.2, 424.4, 424.6, 424.7; 264/45.1, 45.8, 46.5

[56] References Cited

U.S. PATENT DOCUMENTS 4,542,214  9/1985  Bechara .................. 544/107

*Primary Examiner*—Rachel Gorr
*Attorney, Agent, or Firm*—Joseph C. Gil; N. Denise Brown

[57] ABSTRACT

A process is described for producing polyurethane moldings by the reaction of compounds of molecular weight 400 to 10,000 which contain at least 2 hydrogen atoms capable of reacting with isocyanates, and optionally chain extenders of molecular weight 32 to 399, with polyisocyanates, optionally in the presence of foaming agents, auxiliary materials and additives, in which defined carbamates are used as activators. The polyurethanes obtained by this process are particularly low in emissions, i.e. are stable in relation to diffusion and exhibit low fogging, and are thus particularly suitable for the production of composite bodies comprising a polyurethane core and at least one further plastic material as an outer layer. Also described is the use of these moldings and composite bodies which are stable in relation to diffusion and which cause low fogging, e.g. as dashboards or door trims in the construction of vehicles, furniture, machines or apparatus.

14 Claims, No Drawings

PROCESS FOR PRODUCING LOW-EMISSION POLYURETHANE MOLDINGS AND COMPOSITE BODIES AND THEIR USE

BACKGROUND OF THE INVENTION

This invention relates to a process for producing low-emission polyurethane moldings, to composite bodies which are stable in relation to diffusion, and to the use of these composite bodies in the construction of vehicles, furniture, machines or apparatus.

Polyurethanes, particularly polyurethane foamed materials, are used in many fields of application, e.g., as components in the construction of furniture or vehicles.

In addition to the polyisocyanate and the polyol component, other low molecular weight compounds, e.g., activators, are usually added during the production of polyurethane materials, in order to match the catalysis of the foaming and cross-linking reactions. Many of these low molecular weight substances which have previously been used as activators tend to result in unwanted diffusion out of the polyurethane material.

The unwanted diffusion of low molecular weight substances out of the polyurethane material can result in other materials, which as composite materials are in direct surface contact with polyurethanes, being damaged by these substances which are diffusing out. In particular, the unwanted diffusion of Lewis bases of the tertiary amine type, which are often used in the production of polyurethane materials, can result in damage to other materials used with polyurethanes in the composite.

Moreover, in the course of producing polyurethanes by foaming in situ, the molding time, which is frequently longer than for injection molding, is a cost disadvantage. A molding time of 0.5 to 1.5 minutes can in fact be achieved by the use of sufficiently large quantities of catalyst. However, this often leads to problems when using the articles. Particularly since the catalysts which have previously been customarily used intensify these unwanted concomitant phenomena, especially when present in higher concentrations.

Furthermore, in the construction of vehicles the unwanted diffusion of low molecular weight substances out of polyurethane materials can lead to what is termed "fogging". The term "fogging" as used herein denotes the condensation of volatile constituents from all the internal trim of the motor vehicle such as, for example, from dashboards, central consoles, door trims or automobile roofs, on the interior surfaces of window glass of the automobile. A light-scattering deposit is thus formed which results in an impairment of visibility, particularly in conditions of poor illumination. Accordingly, the diffusion behavior of the additives used in polyurethane production is currently of particular importance in vehicle construction.

In addition, materials used in the interior space of an automobile are subjected to severe thermal loading. In this connection, dashboards are subject to particularly severe thermal loading, since the strongly curved windscreens which are presently used in automobile construction act like convergent lenses, and thus, heat the region of the dashboard situated behind them very strongly. Presently, dashboards are also produced from a foamed polyurethane molding, often in combination with a PVC (polyvinyl chloride) and/or ABS (acrylonitrile/butadiene/styrene) outer sheet. In addition to the previously mentioned "fogging effect", low molecular weight substances diffusing out of the polyurethane material may possibly cause damage, under these extreme conditions of thermal loading and heat, to this combination of materials which is employed in automobile interiors. Therefore, it is particularly desirable in vehicle construction to use, in combination with other materials, those polyurethane materials which are particularly stable in relation to diffusion and low in fogging.

A further problem of foaming in situ with short reaction times is that the gas produced during the gassing reaction is liberated too rapidly, and thus, results in too high a pressure in the tool. In many cases, this leads to deformations of or even cracks in the foam, since the strength of the polyurethane polymer is not yet sufficient to maintain stable contours of the foamed material formed.

Thus, the aim of further development work has been to provide foam systems with which the final values of the mechanical strength are achieved more rapidly, without this leading, during catalysis, to problems due to the fogging or ageing of outer layers or to damage to the molded parts on their removal from the mold as a result of a shortened time to demolding.

The object of the present invention was therefore to provide a process for producing low-emission, rapidly demoldable moldings. Another object of the invention was to provide composite bodies comprising a polyurethane core and at least one further plastic material as the outer layer, which consist of a polyurethane core which is particularly stable towards diffusion and which is thus particularly suitable for use in vehicle construction.

Surprisingly, it has now been found that polyurethanes which are particularly low in emissions and low in fogging can be produced with a short molding time if special low molecular weight carbamates are used as activators during the production of the polyurethanes.

SUMMARY OF THE INVENTION

The present invention relates to a process for the production of a polyurethane by reacting
A) one or more polyisocyanates, with
B) an isocyanate-reactive component comprising:
  1) one or more organic compounds having a molecular weight of about 400 to 10,000, and containing at least 2 hydrogen atoms capable of reacting with isocyanates, and
  2) optionally, one or more chain extenders having a molecular weight of about 32 to 399, in the presence of
C) at least one activator selected from the group consisting of:
  1) a carbamate corresponding to the general formula (I):

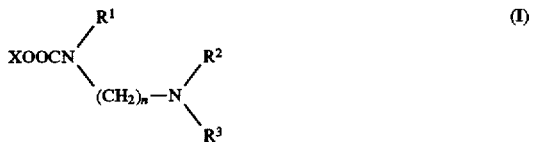

wherein:
  X represents hydrogen or an element of the first main group of the periodic table,
  n is an integer between 1 and 12,
  $R^1$ represents hydrogen, an alkyl radical containing 1 to 6 carbon atoms, or an N,N-dimethylaminoalkyl radical of formula $-(CH_2)_m N(CH_3)_2$, wherein m is an integer between 1 and 6, and
  $R^2$, $R^3$ each represent an alkyl radical containing 1 to 6 carbon atoms, wherein $R^2$ and $R^3$ may be the same or different;

2) a carbamate corresponding to the general formula (II):

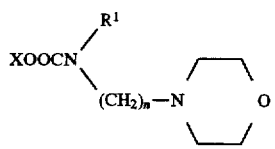 (II)

wherein:
X represents hydrogen or an element of the first main group of the periodic table,
n is an integer between 1 and 12, and
$R^1$ represents hydrogen, an alkyl radical containing 1 to 6 carbon atoms, or an N,N-dimethylaminoalkyl radical of formula —$(CH_2)_m N(CH_3)_2$, wherein m is an integer between 1 and 6;

3) a carbamate corresponding to the general formula (III)

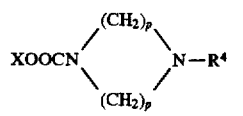 (III)

wherein:
X represents hydrogen or an element of the first main group of the periodic table,
p is an integer between 2 and 4, and
$R^4$ represents an alkyl radical containing 1 to 2 carbon atoms, and 4) a carbamate corresponding to the general formula (IV):

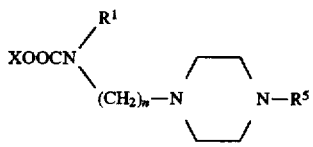 (IV)

wherein:
X represents hydrogen or an element of the first main group of the periodic table,
n is an integer between 1 and 12,
$R^1$ represents hydrogen, an alkyl radical containing 1 to 6 carbon atoms, or an N,N-dimethylaminoalkyl radical of formula —$(CH_2)_m N(CH_3)_2$, wherein m is an integer between 1 and 6, and
$R^5$ represents an alkyl radical containing 1 to 4 carbon atoms, or a carboxyl radical of formula —$(CH_2)_q NR^1COOX$, where q is an integer between 1 and 6 and $R^1$ and X have the given meanings above.

It is also possible to use mixtures of these carbamate activators.

It is also possible that the above reaction occurs in the presence of D) one or more foaming agents, auxiliary agents, or other additives. The presence of any/all of these components D) is optional in the process of the present invention.

Despite their small molecular sizes, the activators used according to the invention exhibit no emissions, i.e., no migration and fogging tendencies. This is manifested, for example, in a reduced damaging action in relation to sensitive decoration materials and cladding materials, such as, PVC, ABS, combinations of PVC and ABS, polyvinyl butyral, polyvinyl acetate, and such as homopolymers and copolymers based on chloroprene, isoprene, styrene, acrylonitrile, dichlorobutadiene, ethylene, propylene and vinyl chloride, which may be present in the form of sheets, coatings, edgings and/or textiles. Due to their surprisingly rapid catalysis, the carbamate activators according to the invention enable a short dwell time in the mold to be achieved.

The activators used in the process according to the invention are all carbamates, and differ only in terms of their differently substituted amino radicals.

In all the compounds of the given formulae, X may either be hydrogen or an element of the first main group, preferably sodium, potassium or lithium.

The preferred carbamates corresponding to formula (I) are those wherein: n is an integer between 1 and 3, $R^1$ is hydrogen or an alkyl radical containing 1 to 2 carbon atoms, or an N,N-dimethylaminoalkyl radical of the given formula where m is an integer between 1 and 3, and $R^2$ and $R^3$ are the same or different alkyl radicals containing 1 to 2 carbon atoms.

Moreover, the preferred carbamates corresponding to formula (II) are those wherein: n is an integer between 1 and 3, and $R^1$ represents hydrogen or an alkyl radical containing 1 to 2 carbon atoms.

Furthermore, preferred carbamates corresponding to formula (III) are those wherein: p represents 2.

Also, preferred carbamates corresponding to formula (IV) are those wherein: n is an integer between 1 and 3, $R^1$ is hydrogen or an alkyl radical containing 1 to 2 carbon atoms, and $R^5$ is an alkyl radical containing 1 to 2 carbon atoms or a carboxyl radical of the given formula, in which q is an integer between 1 and 3.

The following carbamates are most preferred in the process according to the invention:

| No. | Formula |
|-----|---------|
| 1 | HOOC—NH—$(CH_2)_3$—$N(CH_3)_2$ |
| 2 | NaOOC—NH—$(CH_2)_3$—$N(CH_3)_2$ |
| 3 | KOOC—NH—$(CH_2)_3$—$N(CH_3)_2$ |
| 4 | HOOC—N[$(CH_2)_3$—$N(CH_3)_2$]$_2$ |
| 5 | NaOOC—N[$(CH_2)_3$—$N(CH_3)_2$]$_2$ |
| 6 | HOOC—N⟨⟩N—CH$_3$ |
| 7 | HOOC—N(CH$_3$)—$(CH_2)_6$—$N(CH_3)_2$ |
| 8 | HOOC—NH—$(CH_2)_3$—N⟨⟩N—CH$_3$ |
| 9 | HOOC—NH—$(CH_2)_3$—N⟨⟩O |
| 10 | NaOOC—NH—$(CH_2)_3$—N⟨⟩N—CH$_3$ |

In addition to these monofunctional carbamates, those of higher functionality are also suitable. Higher functional carbamates, include, for example, those corresponding to formula (IV), wherein: $R^5$ represents —$(CH_2)_q NR^1 COOX$, with the given meanings for q, $R^1$ and X as set forth hereinabove. The following compound is an example of this type of carbamate, in which $R^1$ and X represent hydrogen:

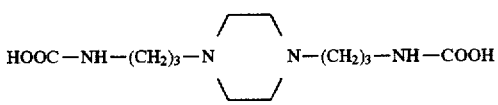

The acidic carbamates Nos. 1, 4, 6 and 7 to 9, as set forth in the preceding table, which are known to be unstable in the presence of isocyanates and which can form amines again, surprisingly exhibit behavior which is completely different from that observed for the amines on which they are based. The amines themselves, on which these acidic carbamates are based, are completely unsuitable for the present process.

Moreover the flow behavior, which is often driven towards a foam which is no longer capable of flowing or a so-called froth by some activators of this type, is not affected at all. In contrast, when using the activators according to the invention, a reaction mixture is formed which advantageously remains flowable and of lower viscosity for a longer time period. However, these reaction mixtures tend to cure rapidly in spite of this.

In the process according to the invention, the activators are used in an amount of 0.01 to 10% by weight, preferably 0.1 to 30% by weight, with respect to 100 parts by weight of the isocyanate-reactive component.

The process according to the invention is conducted in the manner which is known in the art for polyurethanes having a hardness range which can extend from flexible to rigid types of foamed materials. Foamed or solid polyurethanes, preferably foamed polyurethane moldings, can be produced according to the invention.

All the auxiliary materials and additives known in the art, such as, for example, release agents, foaming agents, fillers and flame retardants, can be used in the process according to the invention. Other activator substances known in the art may also optionally be used.

Water and all the organic foaming agents which are customary for this purpose are suitable as the foaming agents in the production of foamed polyurethanes.

Thus, the present invention provides a process for the production of polyurethane plastics by reacting A) one or more organic polyisocyanates, with B) an isocyanate-reactive component comprising:

1) one or more compounds having a molecular weight of about 400 to 10,000, and containing at least 2 hydrogen atoms capable of reacting with isocyanates, and 2) optionally, one or more chain extenders having a molecular weight of about 32 to 399, and containing at least 2 hydrogen atoms capable of reacting with isocyanates, in the presence of C) carbamates of the given formula as activators, and, optionally D) auxiliary agents, additives, and foaming agents comprising water and/or low-boiling hydrocarbons.

The following are used as starting components for the process of the present invention.

Suitable polyisocyanates A) include aliphatic, cycloaliphatic, araliphatic, aromatic and heterocyclic polyisocyanates, such as those described, for example, by W. Siefgen in Justus Liebigs Annalen der Chemie, 362, pages 75 to 136, for example those of general formula $Q(NCO)_n$, wherein n is 2 to 5, preferably 2 to 3, and Q represents an aliphatic hydrocarbon radical containing 2 to 18, preferably 6 to 10 carbon atoms, a cycloaliphatic hydrocarbon radical containing 4 to 15, preferably 5 to 10 carbon atoms, or an aromatic hydrocarbon radical containing 6 to 15, preferably 6 to 13 carbon atoms.

In general, the polyisocyanates which are particularly preferred are those which are readily accessible industrially. These include compounds such as toluene 2,4- and 2,6-diisocyanate, for example, as well as any mixtures of these isomers ("TDI"), diphenylmethane diisocyanate ("MDI") and polyphenyl polymethylene polyisocyanates such as those which are produced by aniline-formaldehyde condensation and subsequent phosgenation, and polyisocyanates containing carbodiimide groups, urethane groups, allophanate groups, isocyanurate groups, urea groups or biuret groups ("modified polyisocyanates"), particularly those modified polyisocyanates which are derived from toluene 2,4- and/or 2,6-diisocyanate or from 4,4- and/or 2,4-diphenylmethane diisocyanate.

Suitable compounds comprising B) the isocyanate-reactive component include 1) organic compounds having molecular weights of about 400 to 10,000 g/mole and which contain at least 2 hydrogen atoms capable of reacting with isocyanates. These are preferably polyether polyols which are known in the art. Polyether polyols are typically the addition products of cyclic ethers such as, for example, ethylene oxide, propylene oxide, styrene oxide or butylene oxide, with starter compounds such as, for example, polyhydroxy compounds such as alkylene glycols, glycerine, trimethylolpropane, pentaerythritol, sorbitol, amines such as ethylenediamine or toluylenediamine, or the starter molecules themselves. Component B) may also comprise 2) one or more organic chain extenders. Suitable chain extenders generally contain from 2 to 8, preferably 2 to 4 hydrogen atoms capable of reacting with isocyanates, and have molecular weights of about 32 to 399. Suitable compounds are described in, for example, DE-OS 2,832,253, pages 19 to 20.

The reaction between the polyisocyanates A) and the isocyanate-reactive component B) may optionally occur in the presence of D) foaming agents, as well as auxiliary agents and/or additives known in the art. Suitable foaming agents for the present invention include water and/or fluoroalkanes and/or low-boiling hydrocarbons. Specifically, low-boiling hydrocarbons include, for example, low-boiling alkanes such as pentane, cycloalkanes such as cyclopentane, and also alkenes. It is, of course, possible to also introduce gases such as, for example, carbon dioxide, into the reaction mixture under pressure.

Auxiliary materials and additives suitable for use in the present invention include, for example, surface-active substances such as emulsifiers and foam stabilizers, retarders, cell regulators of the type known in the art such as paraffins, fatty alcohols or dimethyl polysiloxanes, as well as pigments or colorants, and flame retardants of the type known in the art, and also stabilizers against the effects of ageing and weathering, softeners and substances with fungistatic and bacteriostatic effects.

Examples of surface-active additives and foam stabilizers which may optionally be used in the present invention, as well as retarders, stabilizers, flame retardants, softeners and colorants, and of substances with fungistatic and bacteriostatic effects, as well as details of the methods of use and mode of action of these additives, are described in the Kunststoff-Handbuch [*Plastics Handbook*], Volume VII, edited by G. Oertel, Carl Hanser Verlag, Munich 1993, e.g., on pages 104 to 127.

The carbamates used as activators in the present invention may be admixed with isocyanate-reactive component B) or added separately with stirring to the reaction mixture.

The present invention also relates to composite bodies comprising a polyurethane core and at least one further plastic material. This process comprises lining all/part of the internal walls of a mold with a plastic sheet, filling the mold with a reaction mixture, allowing the mixture to fully react, and removing the composite body from the mold, wherein the reaction mixture comprises A) one or more polyisocyanates, B) an isocyanate-reactive component comprising 1) one or more organic compounds having a molecular weight of about 400 to 10,000 and containing at least 2 hydrogen atoms capable of reacting with isocyanates, and C) an activator comprising one of the carbamates corresponding to formulae (I) through (IV) described hereinabove.

The composite bodies produced in accordance with the present invention are characterized in that, due to the low-diffusion polyurethane cores, practically no damage of the outer plastic layers can be ascertained due to the possibility of low molecular weight compounds diffusing out of the polyurethane. Thus, these composite bodies can also be subjected to very high thermal loadings. The composite bodies according to the invention preferably contain outer plastic layers of PVC, ABS, mixtures of PVC and ABS, polyvinyl acetate, polyvinyl butyral, copolymers and homopolymers based on vinyl chloride, vinylidene chloride, styrene, butadiene, isoprene, chloroprene, dichlorobutadiene, ethylene, propylene or acrylonitrile in the form of sheets, coatings, edgings and textiles.

The composite bodies according to the invention most typically contain the polyurethane core in the form of a foamed backing. Examples of composite bodies of this type include moldings used in vehicle construction, such as, for example, dashboards, arm rests, consoles, head-rests, automobile roofs, coverings used in private cars, automobile seats and door trims.

The present invention further relates to a process for producing these composite bodies, which exist in a sandwich form of construction. In this respect, the process according to the invention for producing the composite bodies can be arranged as a deposition or as a cladding construction process. Both the deposition and the cladding modes of construction are known in the art.

In the deposition process (filling mode of construction) two half shells (e.g., outer layers of fibre-reinforced plastics) are prefabricated, placed in a tool and the hollow space between the shells is foamed with a PUR foam according to the invention. In the cladding mode of construction, a core of PUR foam according to the invention is first placed in a tool and is then clad with a suitable cladding material, e.g., with fibre-reinforced epoxy resins or unsaturated polyester resins. The cladding mode of construction is preferred for the production of the sandwich moldings according to the invention.

The present invention also relates to the use of the polyurethane moldings or composite bodies described above in the construction of vehicles, furniture, machines and apparatus. Polyurethane composite bodies according to the invention are preferably used in vehicle construction, particularly in the interior space of motor vehicles.

The polyurethane moldings and composite bodies according to the invention are very low in emissions. These polyurethane moldings and composite bodies are stable with regard to diffusion and result in extremely low fogging, since practically no low molecular weight substances diffuse out of the polyurethane backing foam produced according to the invention. Thus, no possible damage can be ascertained to the overlying or underlying outer layers and no unwanted deposit can be ascertained on the internal surfaces of the private car window glasses, even under severe thermal loading.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

A) Preparation of carbamates

Example 1

The carbamate of the formula:

$$HOOC-NH(CH_2)_3-N(CH_3)_2$$

was prepared by reacting 102 g (1 mole) dimethylaminopropylamine with 44 g (1 mole) carbon dioxide in 146 g water. The 50% solution of this carbamate was characterized by:

an amine number=390, calculated=384;

an acid number=200, calculated=192.

Example 2

The sodium salt of the carbamate having the formula:

$$NaOOC-NH(CH_2)_3-N(CH_3)_2$$

was prepared by reacting 102 g (1 mole) dimethylaminopropylamine and 44 g (1 mole) carbon dioxide; the carbamate was converted into the sodium salt by adding 40 g (1 mole) NaOH in the presence of 312 g water. The 35% solution of this sodium salt of the carbamate was characterized by:

an amine number=125, calculated=117.

Example 3

The potassium salt of the carbamate corresponding to the formula:

$$KOOC-NH(CH_2)_3-N(CH_3)_2$$

was prepared by reacting 102 g (1 mole) dimethylaminopropylamine and 44 g (1 mole) carbon dioxide to yield the carbamate; the carbamate was then converted into the K salt by adding 56 g (1 mole) KOH in the presence of 277.5 g water. The 40% solution was characterized by:

an amine number=130, calculated=121.

Example 4

A carbamate corresponding to the formula:

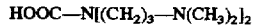

$$HOOC-N[(CH_2)_3-N(CH_3)_2]_2$$

was prepared by reacting 187 g (1 mole) bis-(dimethylaminopropyl)-amine with 44 g (1 mole) carbon dioxide in the presence of 231 g water. The 50% solution of carbamate was characterized by:

an amine number=340, calculated=364;

an acid number=138, calculated=122.

Example 5

The sodium salt of a carbamate corresponding to the formula:

was prepared by reacting 187 g (1 mole) bis-(dimethylaminopropyl)-amine with 44 g (1 mole) carbon dioxide to yield the carbamate; the carbamate was then converted into the Na salt by adding 40 g (1 mole) NaOH in the presence of 261 g water. The 40% solution of the sodium salt of the carbamate was characterized by:

an amine number=188, calculated=177.

Example 6

A carbamate corresponding to the formula:

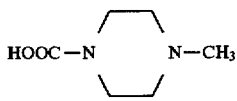

was prepared by reacting 100 g (1 mole) N-methylpiperazine with 44 g (1 mole) carbon dioxide in the presence of 144 g water. The resultant 50% solution of carbamate was characterized by:

an amine number=410, calculated=390;

an acid number=180, calculated=194.

Example 7

A carbamate corresponding to the formula:

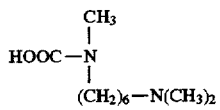

was prepared by reacting 158 g (1 mole) N,N',N"-trimethylhexamethyl-enediamine with 44 g (1 mole) carbon dioxide in the presence of 202 g water. The resultant 50% solution of carbamate was characterized by:

an amine number=280, calculated=277;

an acid number=143, calculated=139.

Example 8

A carbamate corresponding to the formula:

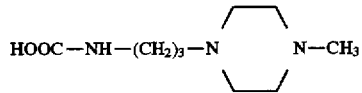

was prepared by reacting 157 g (1 mole) 3-aminopropylmethylpiperazine with 44 g (1 mole) carbon dioxide in the presence of 201 g water. The resultant 50% solution of carbamate was characterized by:

an amine number=410, calculated=418;

an acid number=145, calculated=139.

B) Production according to the invention of polyurethanes
Description of raw materials Polyether Polyol 1: a polyether polyol having an OH number of 28, started on trimethylolpropane and having 17% ethylene oxide and 83% propylene oxide, and at least 80% by wt. of primary OH groups.

Polyether Polyol 2: a grafted polyether polyol based on Polyether Polyol 1, containing 20% by wt. of solids wherein the solids comprise styrene and acrylonitrile in a wt. ratio of 40:60.

Polyisocyanate 1: Polyisocyanate with an NCO-content of 31.0% by weight is a mixture of polyisocyanates from the diisocyanatodiphenyl-methane type with 60% monomeric diisocyanatodiphenyl-methane isomers and 40% polymeric diisocyanatodiphenyl-methane isomers. (Desmodur 44V20 of Bayer AG)

Black Paste N: Dispersion of 20 parts of carbon black and 80 parts of a polyetherpolyole having an OH-number of 35 started on trimethylolpropane and having 13.5% ethylene oxide and 86.5% propylene oxide and 80% by weight of primare OH-groups.

The polyurethane moldings were produced by a method and using a test technique as described in J. Cell. Plast. Vol. 24, pages 284–298, (1988), the disclosure of which is herein incorporated by reference.

Evaluation of the moldings produced according to the invention

The complete formation of the polymer skeleton, which correlates with the hardness of the polymer matrix, can be considered as a criterion for the removal of the moldings from the mold. The hardness can be measured during the reaction time with respect to its final value via the indentation hardness, for example. Based on experience, a molding such as a dashboard can be removed and processed further when it has reached about 90% of its final hardness. Processing problems, such as, for example, indent marks when handling are thus no longer apparent.

Test criteria

1. Hardening behavior

A mixture of raw materials was processed by manually mixing and then introducing the mixture into a metal tool of the approximate size of 200×200×40 mm. The tool was previously heated to about 40° C. The decrease in the indentation hardness measurement in mm or this value as a percentage of the value of the final hardness was then determined for these test specimens with corresponding catalysis. For this purpose, a weight of 1100 g on an 8 mm plate was applied to the foamed materials and the respective depth of indentation after 30 seconds was determined as a measure of the progress of the reaction. The times of measurement were at 3, 5, 10, 20, 30 and 45 minutes. The results are shown in Table 2.

2. Ageing behavior

The ageing behavior of the foam formed on an outer layer was determined. For this purpose, the size of the outer layer was 100×100 mm (length and width) and a thickness of 0.8 mm. The outer layers tested were:

sheeting type A: a PVC (polyvinyl chloride) membrane; commercially available as CZ3; supplied by LVM, Tessenderlo, Belgium, and sheeting type B: a PVC/ABS (polyvinyl chloride/acrylonitrile-butadiene-styrene) membrane; commercially available as LK 55; supplied by Benecke, Hanover, Germany The results are shown in Table 3.

Thermal loading was in a circulating air drying oven for 500 hours at 120° C.

For this purpose, the sheets were provided with a foam backing in a metal tool of the size 200×200×40 mm, which was previously heated to 40° C. in a mold and which had a corresponding recess for the sheets, and the composits A-PUR-foam and B-PUR-foam were then subjected to thermal loading.

3. Fogging behavior

Fogging properties of materials used for the interior trim of motor vehicles were assessed in accordance with DIN 75 201. Two methods are described therein:

Method A—a reflectometric method; provides a measurement of the residual gloss.

A test specimen of material having dimensions of 80 mm diameter and 10 mm thickness, was held for 3 hours in a thermostatted vessel (100° C.). This vessel was sealed with a specially cleaned glass plate which was likewise thermostatted (20° C.).

Constituents which are capable of evaporating and condensing over the temperature interval from 20° to 100° C. were deposited on the cooled glass plate and reduced the degree of reflection compared with a control sample.

Method B—gravimetric method

A test specimen having the same dimensions as described in Method A above was kept in the apparatus described in Method A above for 16 hours. A cooled aluminium foil (20° C.) was used as the condensation surface. The weight of constituents which condensed on the foil, minus the absorbed water, was determined by means of a differential weighing. The speciman 200×200×40 mm was cutted in four parts of 10 mm height and from the middle a specimen of 80 mm diameter was stamped out.

The fogging behavior, as reported in Table 4, was determined by Method B. The amount of deposit was determined in mg.

A foam produced using dimethylaminopropylamine as the activator under conditions which were otherwise identical was employed as a comparison with the prior art.

Example 9

(Foamed Materials 1 to 3):

Three foams were prepared in accordance with the process described hereinabove, from the various components described above. The formulations of these three (3) foams was as shown in Table 1 below.

TABLE 1

| Formulation | 1 | 2 | 3 |
| --- | --- | --- | --- |
| Polyol 1 | 79 | 79 | 79 |
| Polyol 2 | 17 | 17 | 17 |
| Activator of Example 1 | 2.84 | — | — |
| Activator of Example 3 | — | 4.11 | — |
| Dimethylaminopropylamine | — | — | 1.0 |
| Water | 1.08 | 0.24 | 2.5 |
| Black Paste N | 0.5 | 0.5 | 0.5 |
| Isocyanate Index | 100 | 100 | 100 |
| Isocyanate 1 | 44.7 | 44.7 | 44.7 |
| Bulk density (kg/m$^3$) | 64 | 68 | 68 |
| Staff-up time (sec) | 8 | 10 | 10 |

TABLE 2

| Hardening behavior | | | |
| --- | --- | --- | --- |
| Formulation No. | 1 | 2 | 3 |
| Hardness or depth of penetration as a % of the final value, after | | | |
| 3 minutes (%) | 86 | 84 | 68 |
| 5 minutes (%) | 90 | 90 | 73 |
| 10 minutes (%) | 95 | 93 | 79 |
| 20 minutes (%) | 95 | 95 | 90 |

TABLE 2-continued

| Hardening behavior | | | |
| --- | --- | --- | --- |
| Formulation No. | 1 | 2 | 3 |
| 30 minutes (%) | 96 | 96 | 93 |
| 45 minutes (%) | 98 | 98 | 95 |
| Depth of penetration after 60 minutes; in mm | 3.3 | 4.0 | 5.0 |

TABLE 3

| Damage to sheeting in terms of ageing behavior | | | |
| --- | --- | --- | --- |
| Formulation No: (in combination with:) | 1 | 2 | 3 |
| Sheeting A | 1* | 1* | 5* |
| Sheeting B | 1* | 1* | 5* |

*assessment

1: completely unaffected with regard to mechanical behavior and color
3: intermediate degree of damage with regard to mechanical behavior and color
5: severe degree of damage with regard to mechanical behavior and color

TABLE 4

| Fogging behavior according to DIN 75 201 (Method B) | | | |
| --- | --- | --- | --- |
| Formulation No: | 1 | 2 | 3 |
| mg. Deposit | 0.2 | 0.3 | 1.2 |

Based on the preceding tests, it is concluded that the activators according to the invention:

a) cause rapid hardening behavior, as shown in Table 2. Thus Foamed Materials 1 and 2 in Table 2 reached 90% of their final hardness in about 5 minutes. In contrast, Foamed Material 3, which was produced with an amine in accordance with the prior art, reached only 73% of its final hardness after 5 minutes. Foamed Material 3 did not reach the 90% value until about 20 minutes. Moreover, there was a clear positive effect on the final hardness or the degree of crosslinking after 60 minutes, as was apparent from the lesser depth of penetration for Foamed Materials 1 and 2 (as shown in Table 2), which for Foamed Material 1 was reduced by about 35% and for Foamed Material 2 was reduced by about 40%, in comparison to Foamed Material 3.

b) result in no damage to the foam-backed sheeting materials A and B being ascertainable after 500 hours at 120 C., as shown in Table 3.

c) exhibit behavior which is characterized by extremely low fogging, as shown in Table 4.

Processing trials with the formulations in high pressure mixer units, which are customary in production technology (described, for example, in the Kunststoff-Handbuch, Volume (VII), edited by G. Oertel, Carl Hanser Verlag, Munich 1993, page 143, et. seq.) showed that molding times less than 60 seconds were achieved for the manufacture of a complete instrument panel.

The catalysis according to the invention thus permits very short molding times in combination with outstanding ageing properties in relation to emissions such as diffusion and fogging.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a polyurethane comprising reacting
   A) one or more organic polyisocyanates, with
   B) an isocyanate-reactive component comprising:
      1) one or more organic compounds having a molecular weight of about 400 to 10,000, and containing at least 2 hydrogen atoms which are capable of reacting with isocyanates, in the presence of
   C) an activator selected from the group consisting of:
      1) a carbamate corresponding to the general formula (I):

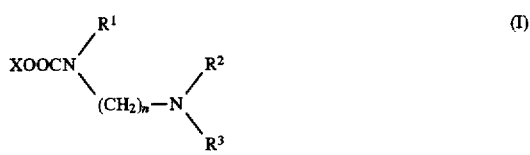

wherein:
   X represents hydrogen or an element of the first main group of the periodic table,
   n is an integer between 1 and 12,
   $R^1$ represents hydrogen, an alkyl radical containing 1 to 6 carbon atoms or an N,N-dimethylaminoalkyl radical of the formula—$(CH_2)_m N(CH_3)_2$, wherein m is an integer between 1 and 6,
   $R^2$, $R^3$ represent identical or different alkyl radicals containing 1 to 6 carbon atoms, 2) a carbamate corresponding to the general formula (II):

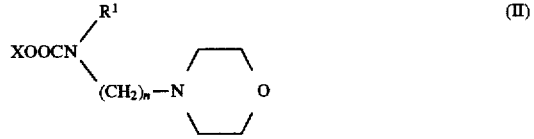

wherein:
   X represents hydrogen or an element of the first main group of the periodic table,
   n is an integer between 1 and 12,
   $R^1$ represents hydrogen, an alkyl radical containing 1 to 6 carbon atoms or an N,N-dimethylaminoalkyl radical of the formula—$(CH_2)_m N(CH_3)_2$, wherein m is an integer between 1 and 6;

3) a carbamate corresponding to the general formula (III):

wherein:
   X represents hydrogen or an element of the first main group of the periodic table,
   p is an integer between 2 and 4, and
   $R^4$ represents an alkyl radical containing 1 to 2 carbon atoms; and 4) a carbamate corresponding to the general formula (IV):

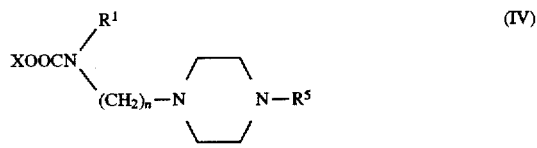

wherein:
   X represents hydrogen or an element of the first main group of the periodic table,
   n is an integer between 1 and 12,
   $R^1$ represents hydrogen, an alkyl radical containing 1 to 6 carbon atoms or an N,N-dimethylaminoalkyl radical of the formula —$(CH_2)_m N(CH_3)_2$, wherein m is an integer between 1 and 6, and
   $R^5$ represents an alkyl radical containing 1 to 4 carbon atoms, or a carboxyl radical of formula —$(CH_2)_q NR^1 COOX$, wherein q is an integer between 1 and 6 and $R^1$ and X have the given meanings.

2. The process of claim 1, wherein B) said isocyanate-reactive component additionally comprises: 2) one or more organic chain extenders having a molecular weight 32 to 399.

3. The process of claim 1, wherein said reaction occurs in the presence of D) foaming agents, auxiliary materials and additives.

4. The process of claim 1, wherein C) said activator comprises 1) a carbamate corresponding to the general formula (I) wherein:
   n is an integer between 1 and 3,
   $R^1$ represents hydrogen, an alkyl radical containing 1 to 2 carbon atoms, or an N,N-dimethylaminoalkyl radical of the formula —$(CH_2)_m N(CH_3)_2$, wherein m is an integer between 1 and 3, and
   $R^2$ and $R^3$ may be identical or different, and each represents an alkyl radical containing 1 to 2 carbon atoms.

5. The process of claim 1, wherein C) said activator comprises 2) a carbamate corresponding to the general formula (II) wherein:
   n is an integer between 1 and 3, and
   $R^1$ represents hydrogen or an alkyl radical containing 1 to 2 carbon atoms.

6. The process of claim 1, wherein C) said activator comprises 3) a carbamate corresponding to the general formula (III) wherein:
   p represents 2.

7. The process of claim 1, wherein C) said activator comprises 4) a carbamate corresponding to the general formula (IV) wherein:
   n is an integer between 1 and 3,
   $R^1$ represents hydrogen or an alkyl radical containing 1 to 2 carbon atoms, and
   $R^5$ represents an alkyl radical containing 1 to 2 carbon atoms, or a carboxyl radical of the formula —$(CH_2)_q NR^1 COOX$, wherein q is an integer between 1 and 3.

8. The process of claim 1, wherein said activators are present in an amount of 0.01 to 10% by weight, based on 100 parts of B) the isocyanate-reactive component.

9. The process of claim 8, wherein said activators are present in an amount of 0.1 to 3.0% by weight, based on 100 parts of B) the isocyanate-reactive component.

10. A foamed polyurethane molding produced by the process of claim 1.

11. In a process for the production of composite bodies comprising the steps of lining all or part of the internal walls of a mold with a plastic sheet, filling the mold with a reaction mixture, allowing the reaction mixture to fully react, and removing the composite body from the mold, wherein said reaction mixture comprises:

A) one or more organic polyisocyanates,

B) an isocyanate-reactive component comprising:
1) one or more organic compounds having a molecular weight of about 400 to 10,000, and containing at least 2 hydrogen atoms which are capable of reacting with isocyanates, and C) an activator selected from the group consisting of:
1) a carbamate corresponding to the general formula (I):

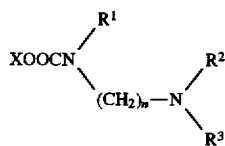

wherein:
X represents hydrogen or an element of the first main group of the periodic table,
n is an integer between 1 and 12,
$R^1$ represents hydrogen, an alkyl radical containing 1 to 6 carbon atoms or an N,N-dimethylaminoalkyl radical of the formula $-(CH_2)_mN(CH_3)_2$, wherein m is an integer between 1 and 6,
$R^2$, $R^3$ represent identical or different alkyl radicals containing 1 to 6 carbon atoms, 2) a carbamate corresponding to the general formula (II):

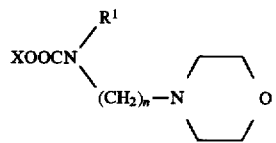

wherein:
X represents hydrogen or an element of the first main group of the periodic table,
n is an integer between 1 and 12,
$R^1$ represents hydrogen, an alkyl radical containing 1 to 6 carbon atoms or an N,N-dimethylaminoalkyl radical of the formula $-(CH_2)_mN(CH_3)_2$, wherein m is an integer between 1 and 6;

3) a carbamate corresponding to the general formula (III):

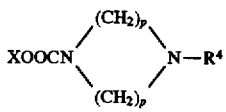

wherein:
X represents hydrogen or an element of the first main group of the periodic table,
p is an integer between 2 and 4, and
$R^4$ represents an alkyl radical containing 1 to 2 carbon atoms; and 4) a carbamate corresponding to the general formula (IV):

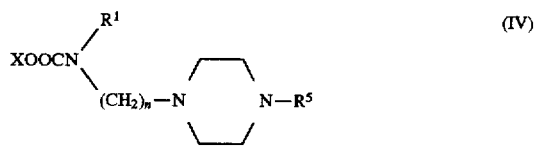

wherein:
X represents hydrogen or an element of the first main group of the periodic table,
n is an integer between 1 and 12,
$R^1$ represents hydrogen, an alkyl radical containing 1 to 6 carbon atoms or an N,N-dimethylaminoalkyl radical of the formula $-(CH_2)_mN(CH_3)_2$, wherein m is an integer between 1 and 6, and
$R^5$ represents an alkyl radical containing 1 to 4 carbon atoms, or a carboxyl radical of formula $-(CH_2)_qNR^1COOX$, wherein q is an integer between 1 and 6 and $R^1$ and X have the given meanings.

12. A composite body produced by the process of claim 11.

13. A composite body produced by the process of claim 11, wherein said plastic sheet comprises PVC, ABS, polyvinyl acetate, polyvinyl butyral, copolymers or homopolymers based on vinyl chloride, vinylidene chloride, styrene, butadiene, isoprene, chloroprene, dichlorobutadiene, polyethylene, polypropylene, acrylonitrile, or mixtures thereof.

14. In a process for the production of a sandwich-type structure comprising applying at least one first plastic substrate and one polyurethane foamed layer to a lower conveyor belt, applying at least one second plastic substrate to an upper conveyor belt, and bringing the second plastic substrate into contact with the foam layer, before curing and by the deflection of the conveyor belt, while the foam layer is still rising on the lower conveyor belt, the improvement wherein said polyurethane foamed layer comprises:

A) one or more organic polyisocyanates,

B) an isocyanate-reactive component comprising:
1) one or more organic compounds having a molecular weight of about 400 to 10,000, and containing at least 2 hydrogen atoms which are capable of reacting with isocyanates, and C) an activator selected from the group consisting of:
1) a carbamate corresponding to the general formula (I):

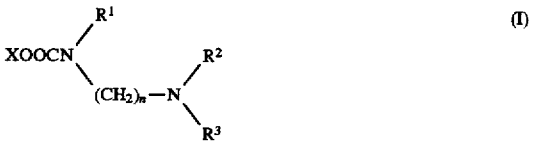

wherein:
X represents hydrogen or an element of the first main group of the periodic table,
n is an integer between 1 and 12,
$R^1$ represents hydrogen, an alkyl radical containing 1 to 6 carbon atoms or an N,N-dimethylaminoalkyl radical of the formula $-(CH_2)_mN(CH_3)_2$, wherein m is an integer between 1 and 6,
$R^2$, $R^3$ represent identical or different alkyl radicals containing 1 to 6 carbon atoms, 2) a carbamate corresponding to the general formula (II):

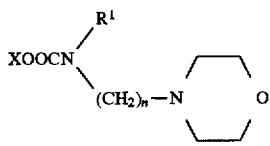 (II)

wherein:
X represents hydrogen or an element of the first main group of the periodic table,
n is an integer between 1 and 12,
$R^1$ represents hydrogen, an alkyl radical containing 1 to 6 carbon atoms or an N,N-dimethylaminoalkyl radical of the formula —$(CH_2)_m N(CH_3)_2$, wherein m is an integer between 1 and 6;

3) a carbamate corresponding to the general formula (III):

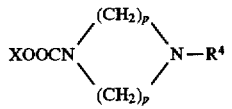 (III)

wherein:
X represents hydrogen or an element of the first main group of the periodic table,
p is an integer between 2 and 4, and
$R^4$ represents an alkyl radical containing 1 to 2 carbon atoms; and 4) a carbamate corresponding to the general formula (IV):

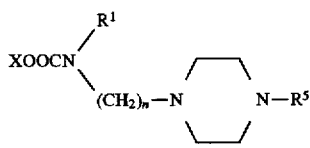 (IV)

wherein:
X represents hydrogen or an element of the first main group of the periodic table, n is an integer between 1 and 12, $R^1$ represents hydrogen, an alkyl radical containing 1 to 6 carbon atoms or an N,N-dimethylaminoalkyl radical of the formula —$(CH_2)_m N(CH_3)_2$, wherein m is an integer between 1 and 6, and $R^5$ represents an alkyl radical containing 1 to 4 carbon atoms, or a carboxyl radical of formula —$(CH_2)_q NR^1 COOX$, wherein q is an integer between 1 and 6 and $R^1$ and X have the given meanings.

* * * * *